United States Patent [19]

Neville et al.

[11] Patent Number: 5,003,046

[45] Date of Patent: * Mar. 26, 1991

[54] MONOCLONAL ANTIBODY PRODUCING HYBRIDOMA AND CORRESPONDING ANTIBODY SPECIFIC FOR HUMAN BREAST FIBROBLAST TUMOR ANTIGEN

[75] Inventors: Alexander M. Neville, Canshalton Beeches; Christopher S. Foster; Paul A. W. Edwards, both of Sutton; Robert A. J. McIlhinney, Carshalton, all of United Kingdom

[73] Assignee: Ludwig Institute for Cancer Research, Zurich, Switzerland

[*] Notice: The portion of the term of this patent subsequent to Mar. 15, 2005 has been disclaimed.

[21] Appl. No.: 137,037

[22] Filed: Dec. 23, 1987

Related U.S. Application Data

[63] Continuation of Ser. No. 558,538, Dec. 5, 1983, Pat. No. 4,731,238.

[30] Foreign Application Priority Data

Dec. 10, 1982 [GB] United Kingdom ................ 8235216

[51] Int. Cl.$^5$ ..................... C07K 15/28; C12N 5/02; A61K 39/395
[52] U.S. Cl. ................................. 530/387; 530/388; 530/395; 530/806; 530/808; 530/828; 435/240.27; 435/172.2; 435/70.21; 424/85.8
[58] Field of Search ............... 424/85.8, 85.91, 88; 435/172.1, 240.27; 530/387, 388

[56] References Cited

U.S. PATENT DOCUMENTS 4,172,124 10/1979 Koprowski et al. ............... 424/85

OTHER PUBLICATIONS

*The Journal of Biological Chemistry*, "Purification of a Human Plasma Membrane Glycoprotein from Human Red Blood Cells by Affinity Chromatography Using a Monoclonal Antibody", vol. 260, No. 1, Issue of Jan. 10, pp. 489–494, 1985, R. A. Jeffrey McIlhinney et al.
Chu, T. et al., *J. Nat. Cancer Institute*, vol. 51, pp. 1119–1122, 1973.
Schlom, J. et al., *Hybridoma in Cancer Diagnosis and Treatment;* Raven Press, New York, 1982, pp. 213–214.
Papsidero, L. et al., *Hybridoma*, vol. 1, pp. 275–282, 1982.
Nuti, M. et al., *Int. J. Cancer*, vol. 29, pp. 539–545, 1982.
McGee, J. et al., *Lancet*, pp. 7–15, 1982.
Edwards, P. et al., *Transplant Proc.*, vol. 12, pp. 398–402, 1980.
Foster, C. et al., *Virchows Arch.*, vol. 394, pp. 279–293, 1982.
Foster, C. et al., *Virchows Arch.*, vol. 394, pp. 295–305, 1982.
Foster, C., *Cancer Treatment Report*, 9, 59–84, 1982.

Primary Examiner—Margaret Moskowitz
Assistant Examiner—Jeff Kushan
Attorney, Agent, or Firm—Felfe & Lynch

[57] ABSTRACT

The invention concerns a novel lymphocyte hybridoma and an antibody which may be generated from the hybridoma. The hybridoma and antibody have the internal designation LICR-LON-Fib 75. The origin, method of preparation and uses are discussed. The antibody has particular application in the diagnosis and treatment of cancer of the breast. A particular therapeutic treatment comprises harvesting a sample of bone marrow from a patient, subjecting the patient to treatment adapted to kill cancerous material including that within the bone marrow (possibly including the normal differentiated haemopoietic cells of the marrow), subjecting some or all of the sample to cytotoxic treatment with the antibody (or a toxin conjugate thereof) adapted to kill cancerous cell lines while leaving viable colony-forming units of bone marrow, and reintroducing the treated sample material to the blood stream of the patient.

2 Claims, No Drawings

MONOCLONAL ANTIBODY PRODUCING HYBRIDOMA AND CORRESPONDING ANTIBODY SPECIFIC FOR HUMAN BREAST FIBROBLAST TUMOR ANTIGEN

This is a continuation of copending application Ser. No. 558,538, filed on Dec. 5, 1983 now U.S. Pat. No. 4,731,238 issued Mar. 15, 1988.

The present invention relates to a novel monoclonal hybridoma, which may be stored as a tissue culture, and to the corresponding antibody which may be generated from the hybridoma and which has important applications in the diagnosis and treatment of cancer, particularly cancer of the breast.

The preferred hybridoma has the internal designation LICR-LON-Fib 75. It is available at the Collection Nationale de Cultures de Micro-Organismes, Institut Pasteur, 128, Rue de Docteur Roux 75724 Paris, France, under the designation CNCM, I-211 (deposit date Dec. 8, 1982).

This invention also includes the antibody expressed by such hybridoma, the antigen specific to the antibody and equivalent structures as set out in the claims forming a part of this specification.

LYMPHOCYTE HYBRIDOMAS

The preferred hybridoma and antibody of this invention, are hereafter referred to shortly as Fib-75 and will have the subscripts H for hybridoma and A for antibody. Fib-75-H is a lymphocyte hybridoma obtained by fusing myeloma cells with normal antibody-secreting cells. Such hybrids are fully discussed in Ref. 1. As discussed in the introduction to that paper, the myelomas are a group of human tumours which have long been considered to be derived by the proliferation of single clones of antibody-forming cells. Naturally-occurring myeloma tumours frequently produce an intact antibody, or specific fragments thereof, although, occasionally, myelomas which are unable to secrete immunoglobulins are also encountered. The demonstration that an analogous tumour could be induced in mice provided the opportunity to produce unlimited amounts of homogeneous immunoglobulin together with a model system with which to investigate the synthesis of antibodies. However, the generation of myelomas making a specific antibody against a pre-defined antigen has never been achieved by this technique. The solution to this problem became apparent in 1975 when Kohler and Milstein (Ref.2) demonstrated that, by fusing myeloma cells with normal antibody-secreting cells, they generated a range of lymphocyte hybridomas which produced antibodies and which, being tumours, immortalized the antigen specificity of the normal parent cells.

The power of the lymphocyte hybridoma system, as devised by Köhler and Milstein, lies in the ability to raise, select and continuously generate specific antibodies to individual determinants following immunization with a heterogeneous and undefined immunogen. The system is extremely sensitive and avoids the initial isolation of a possibly useful antigen—an essential procedure in the production of conventional antisera. It also avoids the numerous steps of adsorption which are frequently required in the production of a conventional heteroantiserum of the desired specificity.

The primary objective of fusing somatic cells with an appropriate cell line is the generation of karyotypically stable hybrids which immortalize specific functions (phenotypes) expressed by normal differential cells. The characteristic phenotype of B-lymphocytes happens to be the generation of identifiable and useful products—antibodies. Similarly, T-lymphocytes express characteristic surface determinants, and somatic cells of non-lymphoid origin are recognized by particular isoenzymes or other specific features. Details of the technical aspects of producing somatic-cell hybrids and generating monoclonal antibodies have recently been reviewed by Galfré and Milstein (Ref.3).

In this specification, the term "determinant" is used synonymously with that of "epitope" to define the precise region or structural configuration of a molecule identified by a monoclonal antibody. The term "antigen" will be reserved to define a complete molecule identified by a conventional heteroantiserum and which may comprise multiple epitopes, each able to be identified by a different monoclonal antibody.

The steps taken in the preparation of the hybridoma and the generation of the monoclonal antibody are conveniently summarized in FIG. 1 of Ref. 1 as shown in FIG. 1 of U.S. Pat. No. 4,731,238.

ORIGIN AND GENERATION OF FIB 75

Fib 75 was isolated as part of a study undertaken with the aim of raising a panel of mouse monoclonal antibodies to human breast fibroblasts. The objectives were to select antibodies which could identify human breast fibroblasts in culture and which (if possible) could be used as cytotoxic reagents. For these purposes, BALB/c mice were immunised with cells obtained from primary monolayer cultures of normal human breast tissue.

A number of hybridomas were isolated in the course of this study in respect of which details have been published in the 1981 Annual Report of the Ludwig Institute For Cancer Research (London Branch) and in the published papers identified hereafter as Refs. 4, 5, 6. As described particularly in Ref. 4 the mouse myeloma utilized was that designated NS1, originating with Dr. C. Milstein (Cambridge, UK). A number of the hybridomas and corresponding antibodies isolated in the course of the study are now well known. However, Fib 75, although referred to e.g. in the aforesaid Annual Report, has not been publicly available before the date of this application.

The general steps of preparation are now described and these follow generally the scheme shown in the drawing.

(i) Preparation of Human Breast Epithelial Organoids

Normal human breast tissues were obtained from a first female patient following reduction mammoplasty surgery performed for cosmetic reasons. So-called 'normal' breast tissues from those regions of mastectomy specimens uninvolved by malignancy were specifically excluded. Attached skin and excess fat were trimmed from the specimens using scissors and the residual tissues diced into pieces no larger than 5 mm cubes. The macerated breast tissues were digested with four volumes of Dulbecco's minimal essential medium (DMEM) containing 0.4 mg/milliliter collagenase (Type 1A, Sigma, Poole, U.K.). Kanamycin (100 μg/ml) and gentamycin (80 μg/ml) were included at all stages of the preparative procedures. Breast epithelial organoids liberated from the intact normal tissues were collected by centrifugation. Precise details of the method have been described in Ref. 7.

(ii) Culture of breast Epithelial Organoids

The breast epithelial organoids from (i) were suspended in Dulbecco's minimal essential medium DMEM containing 10% (v/v) foetal calf serum (Gibco) and Kanamycin (100 μg/ml). The suspensions were plated-out into capped tissue-culture flasks (Nunc., Inter Med., 75 cm² surface area) and incubated at 37° C. in an atmosphere of 100% humidity and 5% $CO_2$ in air.

The DMEM medium surrounding the serum cells and organoids which had attached during the first 48 hours was replaced on alternate days by fresh identical medium. These cultures were maintained for at least five weeks. At the end of this period, the cultures comprised interlacing bundles of fusiform cells (fibroblasts). Cells having a cuboidal appearance (epithelial cells) had almost totally disappeared from these cultures.

(iii) Immunisation of Mice

Culture medium was decanted from the monolayer cell-cultures and the cells were rinsed briefly with sterile normal saline to remove adsorbed foetal calf serum. The attached cells were scraped from the culture-flask with a clean soft rubber spatula. The cells from each 75 cm² flask were suspended in 1 ml sterile normal saline. To this suspension was added 0.5 ml Freund's complete adjuvant and an emulsion prepared using a Vortex (Trade Mark) Mixer. 0.5 ml of this mixture was injected, subcutaneously into each of three female BALB/c mice.

7 days after the primary immunisation, the mice were boosted by an intraperitoneal injection of such cells but obtained from a second female patient and prepared in a manner similar to that already described.

(iv) Fusion 3 days after the mice had been boosted with immunogen, the spleen from one animal was removed, disaggregated and then fused in the presence of poly(ethylene glycol) (PEG) with cells of the murine myeloma NSI (Refs. 3 and 4) using the method description in ref. 5. Hybrid cells were selected using medium containing hypoxanthine, aminopterin and thyimidine according to the techniques of Littlefield (1964) (Ref.8). Hybridoma colonies were grown from the outset in semisolid 0.25% (w/v) agar.

(v) Primary Screening of Hybrids 10 days after the fusion, tissue-culture supernatants were assayed for specific binding to cultivated breast fibroblasts. The fibroblasts (fusiform cells) were obtained from normal human breast by the method previously described (see (ii) above). Cells from a third patient were employed as the source of these cells. One week prior to screening, cells from each 75 cm² plate were resuspended by trypsin and divided equally between the wells of two 24-well (Costar) tissue-culture plates. The cells were cultured in DMEM and under the conditions previously described in (i) above.

Duplicate 100 μl aliquots of each hybridoma culture supernatants were incubated with the 'target' fibroblasts. Bound antibodies were identified using an $^{125}I$-labelled affinity purified rabbit anti-mouse immunoglobulin G (Sera Lab.) (Ref.9).

Colonies from positive wells were picked from the agar and cultured separately. 7 days later, positive colonies were identified using an identical binding-assay.

(vi) Immunohistochemistry

Culture supernatants from positive colonies were concentrated tenfold using Amicon (Trade Mark) B125 filtration chambers. The concentrated supernatants were screened for immunohistochemical binding to normal human tissues using the indirect immunophosphatase technique (Ref.5, p.281(v), Ref.7).

(vii) Selection and Cloning of 'Fib 75'

The binding assays and immunohistochemical studies indicated that the antibody designated LICR-LON-FIB75 bound to many normal human tissues, including the milk fat globule membrane of human breast origin. Single hybridoma cells producing this antibody were cloned by limiting dilution (Ref.10) grown up as separate individual colonies in tissue-culture, and the colonies producing the Fib-75 antibody were identified by binding to the MFGM (human milk fat globule membrane) using the technique previously described (Ref.5 p.281(iv)).

(viii) Antibody Collection and Purification

Cells of the hybridoma Fib-75-H were injected into the peritoneal cavity of BALB/c-mice previously treated with the mineral oil Pristane (Trade Mark) (2,6,10,14-tetramethylpentadecane) (Ref.1. p.67). The proliferating hybridoma cells caused the production of ascites within the peritoneal cavities and this was harvested as it developed.

The monoclonal antibody Fib-75-A was precipitated from the ascitic fluid using ammonium sulphate at 45% (w/v) saturation. The precipitate was dialysed against 50 mM Tris(pH 8.0) and then passaged through a Protein-A Sepharose column. The column was washed in 120 mM phosphate buffer containing 0.15M NaCl until the optical density at 280 nm was zero. The proteins adsorbed by the Protein-A were eluted with 50 mM citrate buffer (pH 6.0). The antibody was collected, dialysed against identical phosphate-buffered saline and stored at −40° C.. Using conventional diffusion-in-agar-gel techniques, the antibody was shown to belong to the IgG2a class. (For general discussion see Ref.11).

(ix) Collection and Purification of the Fib-75 Antigen from Human Red Blood Cells Following the procedure described in Ref.12, the precipitated and dialysed antibody Fib-75-A was coupled to CNBr-activated Sepharose 4B at 10 mg antibody protein per Gramme of beads. Red blood cells were washed and the membrane-ghosts prepared from them by lysis using 10 mM Tris (pH 8.0). The ghosts were dissolved in 50 mM Tris (pH 8.0) containing 0.15 M NaCl and 1% sodium deoxycholate. The Sepharose-coupled FIB-75-A was packed into a chromatography column, and the red blood cell ghost-lysate pumped through it. The column was washed until the optical density at 280 nm was zero. Then the proteins adsorbed by the column were eluted with 50 mM diethylamine buffer (pH 11.0). The protein peak was collected and precipitated with acetic acid. The deoxycholate was removed using ethanol. This yielded approximately 200 μg of antigen per $10^{12}$ red blood cells.

Early studies indicate that the antigen was a glycoprotein with a molecular weight as determined by electrophoresis in polyacrylamide gel of approximately 19,500 daltons.

Later studies showed that the purified molecule had a molecular weight of 19,000±700D based on seven estimations on 10% SDS polyacrylamide gels and appeared to be uncontaminated by other ghost proteins.

Amino-Acid Analysis

Samples (25 μg) of the purified antigen were hydrolysed in 6N HCl for 18 hrs at 60° C. in evacuated glass tubes. The samples were freeze dried, dissolved in distilled water and frezze dried again prior to analysis on a Biotronic (Trade Mark) LC 2000 aminoacid analyser, using norleucine as an internal standard.

REACTIONS AND POTENTIAL OF FIB 75-A

The results from two independent preparations of the antigen are shown in Table 1. The results indicate that the protein is relatively rich in glutamate, aspartate, leucine and valine, relatively poor in methionine and contains no detectable proline.

Carbohydrate Analysis

Samples (100 μg) of the purified protein were analysed for their sugar content as described by Clamp et al (25) on a Perkin Elmer 200 gas chromatograph using D-mannitol as an internal standard.

The analysis (Table 2) from 3 independent preparations showed that the protein was heavily glycosylated (approximately 30% by weight) and that it was rich in galactose and glucosamine.

TABLE 1

Amino acid composition of the purified Fib 75. A binding glycoprotein.

| Amino acid | Amino acids/100 residues | |
|---|---|---|
| | Preparation I | Preparation II |
| Asx | 18.6 | 16.4 |
| Glx | 12.4 | 12.7 |
| Thr | 6.7 | 6.4 |
| Ser | 4.0 | 4.4 |
| Pro | 0 | 0 |
| Gly | 3.1 | 3.0 |
| Ala | 5.7 | 5.9 |
| Cys | 3.9 | 3.9 |
| Val | 10.3 | 9.2 |
| Met | 0.9 | 1.1 |
| Ileu | 1.2 | 1.5 |
| Leu | 10.0 | 10.0 |
| Tyr | 3.73 | 4.4 |
| Phe | 5.9 | 6.3 |
| Lys | 8.0 | 8.4 |
| His | 2.4 | 2.4 |
| Arg | 3.1 | 3.6 |
| Trp | ND | ND |

TABLE 2

Sugar Composition of Purified Fib 75. A Binding Protein

| Sugar | Carbohydrate nmols/mg protein | | |
|---|---|---|---|
| | Preparation I | Preparation II | Preparation III |
| Fucose | 171 | 157 | 114 |
| Mannose | 269 | 266 | 169 |
| Galactose | 443 | 353 | 305 |
| Glucose | 36 | 30 | 57 |
| Galactosamine | 42 | 37 | 28 |
| Glucosamine | 621 | 515 | 463 |
| Sialic acid* | 108 | 98 | 95 |
| % by weight | 33.8 | 28.5 | 24.1 |

*Possibly inaccurate

Immunohistochemical staining of a variety of human tissues by Fib-75-A has been conducted (Ref.5) and the results are summarised in Table 3. The epitope has been found to be present on most differentiated human normal and neoplastic cells. All breast cancers examined reacted positively although there was some heterogeneity of staining of malignant cells in tissue sections. However, there was uniform staining of all malignant cells in effusions and tumour cell lines.

Of considerable importance is the absence of reaction with lymphocytes and colony forming units of human bone marrow.

TABLE 3

Human Tissues Reacting with Fib-75-A

| Positive | Neoplastic |
|---|---|
| | Differentiated Human Tumour Cell Lines* for example: |
| | MCF-7,MDA, EJ, BARON, ZR, PAPIOU } Refs. 13, 14, 17. |
| | Human Breast and other Carcinomas |
| | Normal |
| | Pulmonary Bronchioles and alveoli |
| | Hepatic portal tracts |
| | Renal glomeruli and tubules |
| | Epidermis and appendages |
| | Blood vessels - endothelium |
| | Uterine smooth muscle |
| | Differentiated bone marrow elements: |
| | Granulocytes, red blood cells. |
| Negative | Undifferentiated germ cell tumour lines* for example: |
| | LICR-LONHT39/7, Tera 1 } Refs. 15, 16, 17. |
| | Lymphocytes |
| | Hepatic parenchyma |
| | Hypernephroma cell line (XK1) |
| | Colony Forming Units of Bone Marrow |

*All cell-lines cultured in vitro in DMEM buffered to 5% $CO_2$ and containing 10% foetal calf serum. No other additives required.

IDENTIFICATION OF FIB-75 AND FIB-75-A

Binding to MFGM, as described in (vii) above, provides a convenient immediate identification assay. Collection and identification of the characteristic antigen as a glycoprotein of 19,500 daltons should normally be conclusive. A further cross check is provided by the immunohistochemical reactions with human tissue summarized in Table 3, since this pattern of reactivity is common to no other known antibody.

Conclusive identification is possible via a competitive binding assay. As discussed in the introduction, the specific determinant or epitope, defining the precise region or structural configuration of the antigen molecule identified by the antibody is not known and could reside in a specific amino acid grouping or, for example, in a particular proteinaceous structural configuration. It is, therefore, in theory possible for other closely similar antibodies to react with the same antigen as obtained from red blood cells. Different antibodies would, of course, be expected to recognize different epitopes and this difference of epitopes can be recognized by conducting a competitive binding assay using radioactively labelled bound antibody. Under equilibrium reaction conditions, the addition of unlabelled antibodies should displace a proportion of the labelled antibody which can then be determined. If the suspect antibody is different, it will recognize a different epitope and, therefore, the equilibrium conditions remain unchanged.

Naturally the 19,000 D glycoprotein antigen described above is peculiar to red blood cells. Antigens expressed by other cells e.g. breast or lung, could be identical or have different characteristics, especially molecular weight, since only the epitope or final determinant is common.

THERAPEUTIC POTENTIAL OF FIB-75

During the past decade, there has been an increased appreciation of the importance of accurate staging of patients with cancer at the time of their initial presentation. This emphasis has resulted in the design of therapeutic regimes more appropriate to the stage of disease than was possible hitherto.

The Applicants have had an interest, for some considerable period of time, in trying to detect "latent" metastases in patients with operable breast cancer at the time of their initial presentation. For this purpose a variety of biochemical methods were used to measure tumour markers predominantly in the plasma but also in the urine. The results of those studies showed conclusively that many patients with overt metastases (end-stage disease) had abnormal tumour marker levels. However, few patients considered to have operable localised primary tumours, but whose subsequent course showed that micrometastases must have been present at that time, had raised values. In longitudinal studies, it was also found that while elevated values did occur in many instances before the overt manifestation of metastases, the lead time created was of the order of only 4–5 months, a time that has no clinical utility.

Accordingly, attempts have been made by the Applicants and their associates (Ref.24) to evolve alternative methods to detect metastatic disease. In this context, morphological immunocytochemical methods have been used to detect tumour cells in the bone marrow of breast cancer patients at the time of their initial presentation. These results have been fully documented in Ref.17 (p.24). Using antibodies to the epithelial membrane antigen (EMA) or more recently monoclonal antibodies to breast cell surfaces (LICR-LON-M8), between 20–30% of patients without apparent evidence of spread beyond the axillary lymph nodes at the time of their initial presentation have been found to have tumour cells in their bone marrow. Preliminary follow-up of those patients has shown overt metastases earlier than in subjects in whom such cells are not demonstrable.

It is hoped that this will provide a new approach to treating breast cancer patients with 'small volume' disease. One regimen would be to subject the patients to a form of high dose chemotherapy. This would kill not only the tumour cells but also the normal marrow population. Hence this therapy only becomes reasonable and rational if it is possible to remove tumour-containing bone marrow from those patients, kill the tumour cells in vitro and then return the cleaned-up bone marrow to the patients once the high dose therapy has been completed.

The therapeutic value of many cytotoxic drugs is limited by their toxicity to heamatopoietic stem cells in the bone marrow. Much larger doses can be given safely if the marrow is harvested before administration of the cytotoxic agent and then reinfused once the drug has been excreted or metabolised. This technique, autologous marrow rescue, has been used to allow administration of high doses of melphalan, cyclophosphamide, BCNU and VP-16-213 in many tumours including leukaemias, melanoma, neuroblastoma and several other solid tumours. However, even if such high-dose therapy is effective, viable tumour cells may be reintroduced into the patient on reinfusion if the marrow is infiltrated by malignant cells which may then provide a source for future relapse.

In those tumours where bone marrow infiltration is common, there is, therefore, considerable interest in a 'clean up' procedure to eliminate malignant cells whilst sparing the bone marrow stem-cells. In the leukemias, such cleaning-up procedures have been carried out using conventional (Ref.18) and monoclonal antibodies (Ref.19) (both with heterologous complement) and with certain cytotoxic drugs (Ref.20).

In this context the monoclonal antibody Fib-75-A may have an important clinical role, since it does not react with colony forming units of normal human bone marrow but has specific cytotoxicity to a number of human epithelial tumour cell lines. Accordingly, cytotoxicity studies were conducted in the absence and presence of bone marrow cells.

Complement Mediated Cytotoxicity

51Cr-release assays according to the method of Brunner et al (Ref.21) together with Trypan Blue exclusive (i.e. viability) estimates were employed in the presence of rabbit complement (RC) (Pel-Freez) to access the degree of cytotoxicity. After preliminary experiments with $1 \times 10^5$ MCF-7 (breast), MDA (Breast) or EJ (Bladder) cells as targets in the presence of $10^7$ bone marrow cells, maximal cell killing was found to be achieved by incubation at 37° C. for 2 hours in the presence of 5 μg Fib-75-A, and aliquots of 200 μl RC added at the beginning and after 1 hour.

Using the above quantities, cytotoxicity was examined on cell lines and malignant effusions (Table 4). The results indicate that no tumour cells are viable after exposure to Fib-75-A and complement except when large clumps (>500 cells) are present.

TABLE 4

CYTOTOXIC EFFECT OF FIB-75 PLUS RABBIT COMPLEMENT ON CELL LINES AND MALIGNANT BREAST CANCER CELLS IN EFFUSIONS[a]

| Cell Source | Number of Experiments | Tumour Cells Alone | % $^{51}$Cr Release Tumour Cells + Bone Marrow Cells[b] | Tumour Cell Viability by Tryptan Blue |
|---|---|---|---|---|
| MALIGNANT CELL LINES | | | | |
| MCF-7 | 5 | 84 (76–92) | ND | 0% |
| MDA | 16 | 83 (68–100) | 77 (59–84) | 0% |
| EJ | 5 | 73 (69–76) | 65 (62–68) | 0% |
| MALIGNANT EFFUSIONS (BREAST CANCER) | | % MALIGNANT CELLS IN FLUID | | |

TABLE 4-continued

CYTOTOXIC EFFECT OF FIB-75 PLUS RABBIT COMPLEMENT ON CELL LINES AND MALIGNANT BREAST CANCER CELLS IN EFFUSIONS[a]

| Cell Source | Number of Experiments | Tumour Cells Alone | % $^{51}$Cr Release Tumour Cells + Bone Marrow Cells[b] | Tumour Cell Viability by Tryptan Blue |
|---|---|---|---|---|
| Patient A | 2 | >90% | 80 | ND | 0% |
| Patient B | | | | | |
| 1st Ascites | 1 | 40% | 25 | ND | 55[e] |
| 2nd Ascites | 1 | >80% | 64 | 52 | 0% |
| Patient C | 1 | 90% | 55 | UNINT[c] | 5% |
| Patient D | 1 | ? | 66 | 51 | LARGE CLUMPS[d] |

Footnotes to Table 4:
[a] The amount of $^{51}$Cr-released into the supernatant (in counts per minute (cmp)) was expressed as a percentage of the maximum release achieved by lysis with 5% NP-40 detergent according to the formula:

$$\% \text{ release} = \frac{\text{experimental cpm} - \text{spontaneous cpm}}{\text{maximal cpm} - \text{spontaneous cpm}}$$

As a control for this experiment cells were incubated with antibody alone and with complement alone. These assays were done in triplicate. In all these experiments 1–5 × $10^5$ target cells were used in a standard volume of 500 μl of tissue culture medium (RPMI 1640 with 2% foetal calf serum).
[b] Nucleated bone marrow cells from human donors were collected in early experiments by separating whole bone marrow over a Ficoll-Hypaque mixture of density 1 · 100 g/ml. This was found to retain most nucleated cells including granulocytes at the interface. 5–10 × $10^5$ nucleated bone marrow cells were resuspended in 0.5 ml medium and 5–10 × $10^4$ labelled target cells added to represent bone marrow infiltrated with 1% of malignant cells. Subsequent results in CFU-C assays showed better preservation if the granulocytes were eliminated by using Ficoll-Hypaque of density 1 · 077 ('Lymphoprep').
[c] Uninterpretable due to very high spontaneous loss of $^{51}$Cr.
[d] Some large clumps (>500 cells) contained some viable cells.
[e] Contamination by mesothelial cells.

Effect on Bone Marrow 'Stem' Cells

With the demonstration of tumour cell killing, it was important to ascertain if the therapy spared the bone marrow cells thereby enabling potential in vivo recovery.

Bone marrow stem-cells were assayed by the standard colony-forming-unit (CFU-C) method (Ref.22) which measures progenitor cells committed to the granulocyte-macrophage series, and also by pluripotential stem-cell assays on CFU-C, erythroid stem-cells (BFU-E), megakaryocytic (Megakar) colony-forming units and mixed colonies of erythroid-myeloid types (Ref.23). The results are shown in Table 5.

TABLE 5
EFFECT OF FIB-75 AND COMPLEMENT ON PLURIPOTENTIAL STEM-CELL ASSAY

| Aliquots of complement added | Bone marrow % survival of | | | |
|---|---|---|---|---|
| | CFU-C | BFU-E | MegaKar | Mixed |
| 1 | 36 | 48 | 22 | 72 |
| 2 | 52 | 45 | 33 | 10 |
| 1 | 95 | 52 | 87 | 25 |
| 2 | 85 | 47 | 62 | 100 |
| 1 | 102 | 70 | 75 | 75 |
| 2 | 90 | 81 | 100 | 200 |

It may be concluded from Table 3 that while CFU-C's may be reduced to approximately 60%, the effect of Fib-75-A and RC as assessed in the pluripotential assay was insignificant.

Effect on Malignant Colony-Forming Cells

Once the $^{51}$Cr-release assays had shown maximal cell killing, plating assays were done to identify any remaining tumour cells still capable of division. EJ (bladder) cells were used because of their high plating efficiency. A minimum of two cells are required to form one identifiable colony at one week. EJ cells were treated with Fib-75-A and complement in suspension, then plated into tissue cultures wells in full growth medium to detect any residual cells capable of division and colony formation.

With aliquots of 1×$10^5$ cells with and without the presence of bone marrow cells, no colonies were seen after 7 days at which time all control wells had achieved confluent growth.

SUMMARY

Autologous marrow rescue is an essential component of high-dose therapy, using either radiation of chemotherapy but it has been recognized that many patients at initial presentation with solid tumours, including breast (Ref.24) and lung carcinomas have marrow infiltration. Since reinfusion of these tumour cells could provide foci for recurrent disease, ways of killing these cells have been investigated.

Complement lysis of tumour cells in vitro has been demonstrated using the Fib-75 antibody. In order to ascertain whether all cancer cells are killed, the experiments included the highly clonogenic cell line, EJ, derived from a human bladder carcinoma and it was demonstrated that clonogenicity was abolished up to a contamination of $10^5$ EJ cells in $10^7$ bone marrow cells. Using the same quantities of antibody and complement on malignant cells derived from patients' effusions, which cannot be grown readily in culture, more than 95% of the cancer cells were killed although large clumps of tumour cells were found to contain viable cells after exposure, presumably due to inadequate penetration of antibody. This problem relevant to the treatment of infiltrated bone marrow, since such large clumps of tumour cells do not occur at this site.

The antibody also binds human complement and although this was a relatively unreliable source of complement or routine assays it does suggest that if any tumour cells binding Fib-75-A are viable at the time of re-infusion, they are likely to be killed in the presence of fresh complement in the patient's plasma.

The quantities of Fib-75-A and rabbit complement used to kill malignant cells depressed the bone marrow CFU-Cs by less than 50%. However the CFU-C assay measures a stem-cell committed to the granulocyte-macrophage series and which is thought to be relatively advanced in the differentiation process. Since mature granulocytes express the Fib-75 antigen strongly it is likely that effect on the CFU-C assay is greater than the effect on the true totipotential stem-cell which cannot, at present, be assayed. The pluripotential stem-cell assays performed tend to support that idea that the less differentiated earlier stem-cells are relatively unaffected.

Absorption of rabbit complement against human blood cells was shown to be necessary in order to prevent the occasional very severe effect on the CFU-C assay which was probably due to heterophile antibody in the rabbit serum and which would therefore be expected to have a non-specific toxic effect on all bone marrow stem-cells.

The results indicated that Fib-75-A mediates complement lysis of tumour cells in bone marrow both effectively and safely. The antibody is not specific to breast carcinoma and could therefore be used in all tumours that bear the Fib-75 antigen provided that tumour cells in the marrow do not occur in very large clumps. The results are sufficiently encouraging to permit the commencement of a high dose therapy programme for breast cancer patients.

Further therapeutic potential

Studies are in hand to conjugate a toxin (e.g. ricin) to Fib-75-A. The antibody-toxin conjugate will be assessed for its effect on model breast tumour cell lines in vitro and its effect on the colony-forming-unit capacity. It is hoped that this will obviate the use of large amounts of rabbit complement.

It is further envisaged that Fib-75-A, in association with complement, or as an antibody-toxin conjugate, may provide a valuable reagent for aiding autologous bone marrow grafting in patients, in particular with breast and oat cell carcinoma, at the time of their initial presentation when they are found to have micrometastatic disease.

Where national jurisdiction permits, the invention is inclusive of methods of therapeutic and diagnostic treatment of humans or animals utilizing the antibody Fib-75-A as described above. In particular the invention is inclusive of a method of treating cancer (especially cancer of the breast) which comprises harvesting a sample of bone marrow from a patient, subjecting the patient to treatment adapted to kill all cancerous material at least within the bone marrow, subjecting some or all of the samples to cytotoxic treatment with Fib-75-A (or a toxin conjugate thereof) adapted to kill cancerous cell lines while leaving viable colony-forming-units of bone marrow, and reintroducing the treated sample material to the blood stream of the patient.

Toxins suitable for conjugation may include e.g. macromolecular toxins such as ricin, abrin, or subunits thereof, drugs such as for example methotrexate and adriamycin, and radio-active isotopes such as iodine 131 and indium 111. Bound isotopes are also useful for localisation. Conjugation of antibodies of a similar nature with toxins is a known procedure cf. Ross et al (26). Conjugation with isotopes is straight forward by well established chemical reactions.

1. Foster, C. S. Lymphocyte hybridomas. Cancer Treatment Reviews (1982) 9, 59–84.
2. Köhler, G. & Milstein, C. (1975). Continuous cultures of fused cells secreting antibody of predefined specificity. Nature 256, 495–497.
3. Galfré, G. & Milstein, C. (1982). Preparation of monoclonal antibodies: strategies and procedures. In: (Langone, J. J. & Vunakis, H. V., eds). Methods in Enzymology, Volume 73(B): Immunochemical Techniques. New York: Academic Press, pp. 1–46.
4. Edwards, P. A. W., Foster, C. S., and McIlhinney, R. A. J. Monoclonal Antibodies to Teratomas and Breast. Transplantation Proceedings, Vol. XII, No. 3 (September), 1980.
5. Foster, C. S., Edwards, P. A. W., Dindale, E. A. and Neville, A. M. 1982. Monoclonal antibodies to the human mammary gland. I. Distribution of determinants in non-neoplastic mammary and extra mammary tissues. Virchow's Archiv. 394, 279–293.
6. Foster, C. S. Edwards, P. A. W., Dinsdale, E. A. and Neville, A. M. 1982. Monoclonal antibodies to the human mammary gland. I Distribution of determinants in non-neoplastic mammary and extra mammary tissues. Virchow's Archiv. 394, 295–305.
7. Foster, C. S., Smith, C. A., Dinsdale, E. A., Monaghan. P. and Neville, A. M. Human Mammary Gland Morphogenesis in vitro: The Growth and Differentiation of Normal Breast Epithelium in Collagen Gel Cultures Defined by Electron Microscopy, Monoclonal Antibodies and Autoradiography. Developmental Biology. (Submitted 2 August 1982, available from 29 November 1982 from the Librarian, Royal Marsden Hospital Library, Sutton, Surrey.
8. Littlefield, J. W. Selection of Hybrids from Matings of Fibroblasts in vitro and their Presumed Recombinants. Science 145, 709–710 (1964).
9. Jensenius, J. C. and Williams, A. F. The Binding of Anti-Immunoglobulin Antibodies to Rat Thymocytes and Thoracic Duct Lymphocytes. Eur. J. Immunol. 4, 91–97 (1974).
10. Paul, S. IN: Cell and Tissue Culture (4th Edition) Livingstone, Edinburgh and London. pp 234–236 (1970).
11. Hybridoma Technology by G. Trincheri, Chapter 8 with special reference to Parasitic Diseases. Published by: UNDP/Word Bank/WHO (1979).
12. Brown, W. R. A., Barclay, N. A., Sunderland, C. A. and Williams, A. F. (1981). Nature, 289: 456–460.
13. Easty D. M., Easty G. C., Cater R. L., Monaghan P., Butler L. J. Ten Human Cell Lines Dervied from Squamous Carcinomas of the Head and Neck. BR. J. Cancer 43: 772–785, 1981.
14. Ellison M. Woodhouse D., Hillyard et al. Immunoreactive Calcitonin Production by human lung carcinoma cells in culture. Br. J. Cancer 32: 373–379, 1975.
15. Colte, S. A., Easty G. C., Neville, A. M., Establishment and properties of human germ cell tumours in tissue culture. Cancer Res. 41: 1422–1428, 1981.
16. McIlhinney R. A. J. Cell Surface Molecules of human teratoma cell lines. Int. J. Andrology Supp. 4: 93–109, 1081.
17. Annual Report (1981) of the Ludwig Institute for Cancer Research (London Branch). paras. 21,22.
18. Netzel B., Rodt H., Haas R. J., Kolb H. J., Thierfelder S. Immunological Conditioning of Bone Marrow for Autotransplantation in Childhood Acute Lymphoblastic Leukemia. Lancet 1: 1330–1332, 1980.
19. Ritz J., Sallan S. E., Bast R. C. et al. Autologous Bone-Marrow Transplantation in CALLA-Positive Acute Lymphoblastic Leukemia After In Vitro Treatment with J5 Monoclonal Antibody and Complement. Lancet 2: 60–63, 1982.

Kaizer, H., Stuart, R. K, Fuller DJ et al. Autologous Bone Marrow Transplantation in Acute Leukemia: Progress Report on a Phase I Study of 4-Hydroperoxy-cyclophosphamide Incubation of Marrow Prior to Cryopreservation. Proc. ASCO 1982, 1-131 (Abstract).

21. Brunner K. T., Mauel J., Cerottini J.-C., Chapuis B. Quantiative Assay of the Lytic Action of Immune Lymphoid Cells on $^{51}$Cr-Labelled Allogeneic Target Cells in Vitro; Inhibition by Isoantibody and by Drugs. Immunology 14: 181–196, 1968.

22. Pike B. L., Robinson W.A. Human Bone Marrow Colony Growth in Agar-Gel. J. Cellular Physiol. 76: 77–84, 1970.

23. Messner H. A., Izaguirre C. A., Jamal N. Identification of T Lymphocytes in Human Mixed Hemopoietic Colonies. Blood 58, 2: 402–405, 1981.

24. Dearnaley D. P., Sloane J. P., Ormerod M. G. et al. Increased Detection of Mammary Carcinoma Cells in Marrow Smears Using Antisera to Epithelial Membrane Antigen. Br. J. Cancer 44: 85–90, 1981.

Clamp, J. R., Bhatti, T. and Chambers, R. E. Determination of Carbohydrate in Biological Materials by Gas Liquid Chromatography. (1971) Meths. Biochem. Anal. 19, 229–250.

26. Ross, W. C. J., Thorpe, P. E., Cumber, A. J., Edwards, D. C., Hinson, C. A. and Davies, A. J. S. Increased Toxicity of Diptheria Toxin for Human Lymphoblastoid Cells following Covalent Linkage to Anti-(human lymphocyte) Globulin or Its F(ab')$_2$ Fragment. (1980) Eur. J. Biochem. 104, 381–390.

We claim:

1. A biologically pure culture of the monoclonal hybridoma designated LICR-LON Fib 75 (CNCM, I-22).

2. The antibody designated LICR-LON-Fib 75 as generated by the hybridoma culture of claim 1.

* * * * *

UNITED STATES PATENT AND TRADEMARK OFFICE
CERTIFICATE OF CORRECTION

PATENT NO. : 5,003,046
DATED : March 26, 1991
INVENTOR(S) : Alexander M. Neville et al.

It is certified that error appears in the above-identified patent and that said Letters Patent is hereby corrected as shown below:

Col. 5, line 10, change "frezze" to --freeze--.

Col. 6, line 37, change "FIB-75" to --FIB-75-H--.

Col. 12, line 5, change "Dindale" to --Dinsdale--.

Col. 14, line 1, change "Clamp" to --25. Clamp--.

Signed and Sealed this

Thirtieth Day of March, 1993

Attest:

STEPHEN G. KUNIN

*Attesting Officer*  Acting Commissioner of Patents and Trademarks